United States Patent [19]

Eppolito

[11] 4,438,764

[45] Mar. 27, 1984

[54] OXYGEN CADDY

[76] Inventor: Salvatore Eppolito, 77 Wert Ave., Trenton, N.J. 08610

[21] Appl. No.: 413,415

[22] Filed: Aug. 31, 1982

Related U.S. Application Data

[63] Continuation-in-part of Ser. No. 255,565, Apr. 20, 1981, Pat. No. 4,383,528.

[51] Int. Cl.$^3$ .......... A61M 16/00

[52] U.S. Cl. .......... 128/205.22; 128/204.18; 224/225; 224/227; 224/210; 224/259; 150/51

[58] Field of Search .......... 128/205.22, 202.13, 128/294.18, 200.24; 224/201, 204, 205, 225, 227, 908, 907, 209, 210, 211, 212, 259, 261, 265; 150/51, DIG. 1

[56] References Cited

U.S. PATENT DOCUMENTS

| | | | |
|---|---|---|---|
| 1,652,387 | 12/1927 | Barber | 150/51 |
| 2,836,234 | 5/1958 | Davis . | |
| 3,396,885 | 8/1968 | Giondi | 150/51 |
| 4,074,839 | 2/1978 | Wood et al. . | |
| 4,133,464 | 1/1979 | Kelty | 224/262 |
| 4,169,550 | 10/1979 | Williams . | |

FOREIGN PATENT DOCUMENTS

| | | |
|---|---|---|
| 199348 | 8/1938 | Switzerland . |

*Primary Examiner*—Henry J. Recla
*Attorney, Agent, or Firm*—Sanford J. Asman

[57] ABSTRACT

The oxygen caddy is a carrier for an oxygen tank of the type used by emergency medical personnel. It includes a fabric case which covers a rigid, protective, supporting frame in which the oxygen tank is held. The case includes pockets in which oxygen delivery means may be stored for use. The oxygen delivery means are attached to the oxygen tank via hoses which extend into the pockets through openings in the case. A shoulder strap is provided in order to allow emergency personnel to carry the oxygen carrier without using his hand, which is then free to carry other equipment.

16 Claims, 8 Drawing Figures

10
27
25
26
14
28
24
16
18
12
38
40
29

27
26
25
28
24
18
21
56
20
58

14
34
36
54
52
35
42
16
25
18
37
39
41
27
24
28
37
39
38
26
29
25

27
25
24
41
26
28
37
16
39
37
20
39
25

OXYGEN CADDY

CROSS-REFERENCE TO RELATED APPLICATION

The present application is a continuation-in-part of co-pending U.S. patent application Ser. No. 255,565 filed Apr. 20, 1981 now U.S. Pat. No. 4,383,528.

BACKGROUND OF THE INVENTION

The present invention relates to a carrier unit, or caddy, for a bottled gas, such as oxygen. In particular, the invention relates to a carrier, called "OXY-CADDY" by its inventor, for portable oxygen tanks and resuscitators of the type used by first aid and emergency squads.

Oxygen contained in metal bottles has long been used for medical purposes. Such bottled oxygen is generally taken to the location of the victim of a medical emergency, such as a choking victim or a heart attack victim.

Heretofore, oxygen bottles, or tanks, of the type with which the present invention is used, were carried in various types of rigid carriers. The reason for using rigid carriers has been to afford protection to the cutoff valve which must be installed on the tank in order to deliver oxygen as it is needed. Such carriers have generally been constructed of wood or metal, and as such, they have been relatively heavy and unwieldy.

Some newer carriers are constructed of plastic, in order to cut down on their weight and to provide a carrying handle which allows the oxygen tank to be carried more easily by emergency personnel. However, various problems have been encountered with the plastic carriers. In particular, they require that the emergency personnel devote a hand to hold the oxygen carrier, which prevents them from carrying something else in that hand. In addition, the plastic carriers have not generally held up well in use.

Generally, emergency personnel carry a lot of equipment in addition to oxygen tanks on their ambulances and emergency vehicles. Due to the increased amount of such equipment, which includes cardiac telemetry equipment and drug kits, amonth many other items, it is desirable to provide an oxygen carrier which can be carried by such personnel, yet which still leaves their hands free to carry other items. In addition, an oxygen carrier which protects the valve or regulator at the top of the oxygen tank is desirable.

Finally, multipurpose regulators are now available which provide for the attachment of multiple oxygen delivery means, including demand valves, aspirators, and inhilators. By way of example, a three-way valve of the type described is presently available for Robertshaw Controls Company, Life Support Products Marketing Group, 333 N. Euclid Way, Anaheim, Calif. 92803.

It would be highly desirable to have an oxygen tank carrier which could be carried by emergency personnel which would make each of the aforementioned oxygen delivery means available for instant use and which would allow the emergency personnel to utilize their hands to carry other equipment onto the scene of the emergency. In addition, it would be highly desirable to have such a unit in which the oxygen bottle could be rapidly changed.

SUMMARY OF THE INVENTION

In accordance with the present invention an oxygen carrier or caddy is provided which is comprised of a rigid frame designed to surround and protect the oxygen bottle and its valve. The frame includes resilient retaining means which securely hold an oxygen bottle which has been lowered down into the frame, yet which permits the rapid removal, and replacement, of oxygen bottles. The frame is covered by a case made of a durable material, such as canvas. The case contains pockets in which the various oxygen delivery means are normally stored. In addition, the oxygen caddy preferable has a shoulder strap which can be slung over the shoulder of the emergency personnel carrying the oxygen in order to leave his hands free for other purposes. Openings in the covering material allow appropriate hoses from the valve to pass directly from the valve into the pockets whereby the oxygen bottle, valve, regulator, and delivery means are fully protected when stored, but are instantly available for use when necessary.

DETAILED DESCRIPTION OF AN EXEMPLARY EMBODIMENT

Figure 1:
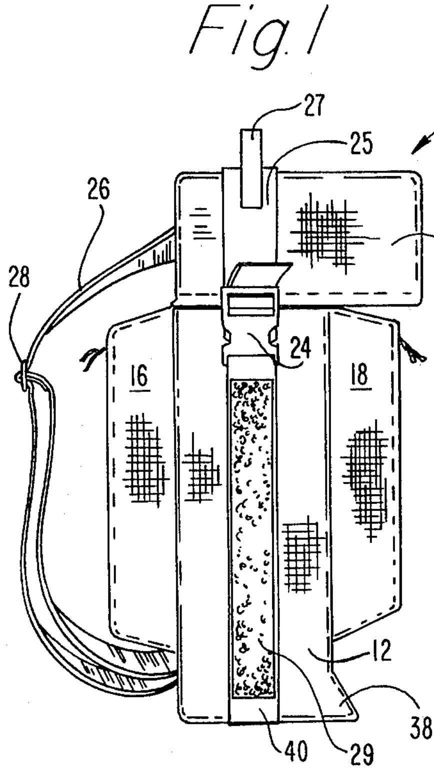
FIG. 1 is a front view of the oxygen caddy of the preferred embodiment of the invention showing the oxygen caddy as it is normally stored.

Referring generally to FIGS. 1–4, the oxygen caddy 10 of the preferred embodiment of the present invention, is shown. The oxygen caddy 10 comprises a case 12 made of a durable covering material, typically a fabric such as canvas or nylon. The case 12 has a top 14 which closes over the top of an oxygen tank 52. On either side of the case 12, there are pockets 16, 18, which have zippers 20, 22, respectively. The purpose of the pockets 16, 18 is to carry oxygen delivery means, as will be seen hereinafter. In the preferred embodiment of the invention, the zippers 20, 22 are used to close the pockets 16, 18, thereby allowing them to be readily opened to expose the oxygen delivery means contained in them, as well be seen more fully hereinafter.

The flap 14, is preferrably closed using a support strap 25 which encircles the oxygen caddy 10. The support strap 25 may be opened using a quick release buckle 24. In the preferred embodiment of the invention, the quick release buckle 24 is Model SR-2 made by FASTEX of Des Plaines, Ill. 60016. That buckle 24 is described more fully in U.S. Pat. No. 4,150,464.

The oxygen caddy 10 further comprises a shoulder strap 26, which is attached to the support strap 25 encircling the oxygen caddy 10. Preferably, the support strap 25 and the shoulder strap 26 are made of a strong, flat material, such as nylon strapping. The shoulder strap 26 preferably includes an adjustment means, such as a buckle 28, which may be used to alter the length of the shoulder strap 26 for the comfort and convenience of the particular individual who will be carrying the oxygen caddy 10. The caddy 10 may be carried either over one's shoulder, using the shoulder strap 26, or by hand, by holding either the shoulder strap 26, or by holding a carrying strap 27 which is attached to the support strap 25 at the top of the oxygen carrier. The carrying strap 27 is also preferably made of a strong, flat material, such as canvas strapping.

With particular reference to FIG. 1, the front of the support strap 25 preferably has a section 29 which is covered with one portion of a hook and loop type fastening material, such as Velcro. In the preferred embodiment of the invention, the section 29 is covered with the loop type of material. The purpose of the section 29 is to provide an easy way for emergency personnel to attach an accessory bag (not shown) to the oxygen caddy 10. Such an accessory bag would, of course, have a section covered with the complementary material, in this case, the hook material, so it could be readily attached to or detached from the oxygen carrier 10. The accessory bag would typically be used to carry drugs, supplies, or equipment.

Figure 2:
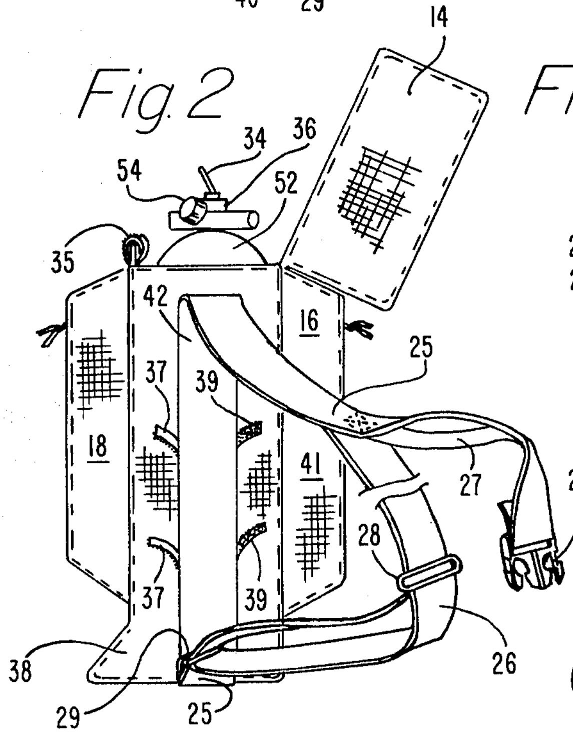
FIG. 2 is a rear view of the oxygen caddy of FIG. 1 with the shoulder strap removed.
Figure 4:
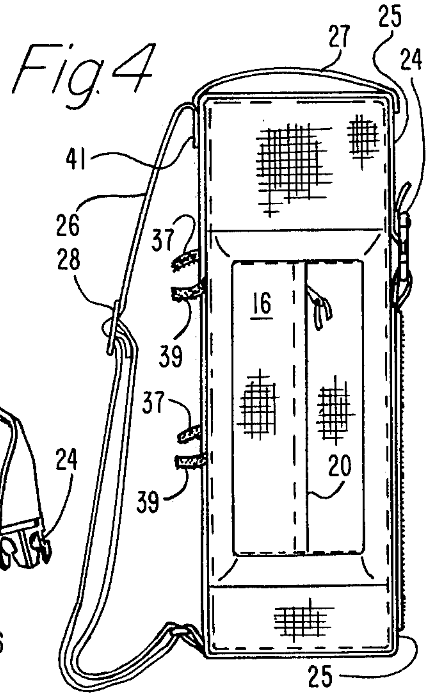
FIG. 4 is view of the left side of the oxygen caddy of FIG. 1.
Figure 6:
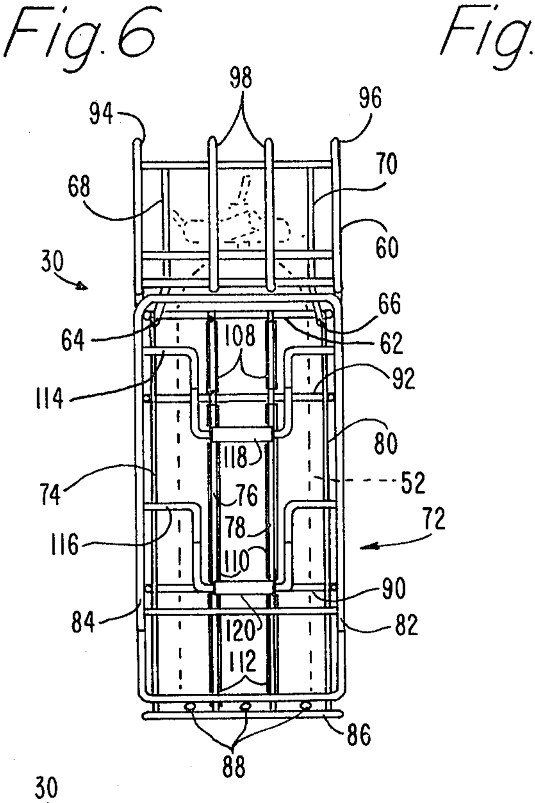
FIG. 6 is a front view of the frame of FIG. 5 holding an oxygen tank.
Figure 7:
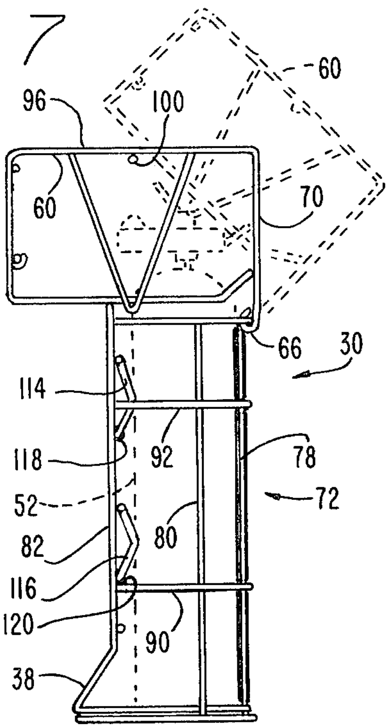
FIG. 7 is a side view of the frame of FIG. 5 with an oxygen tank shown in shadow.
Figure 5:
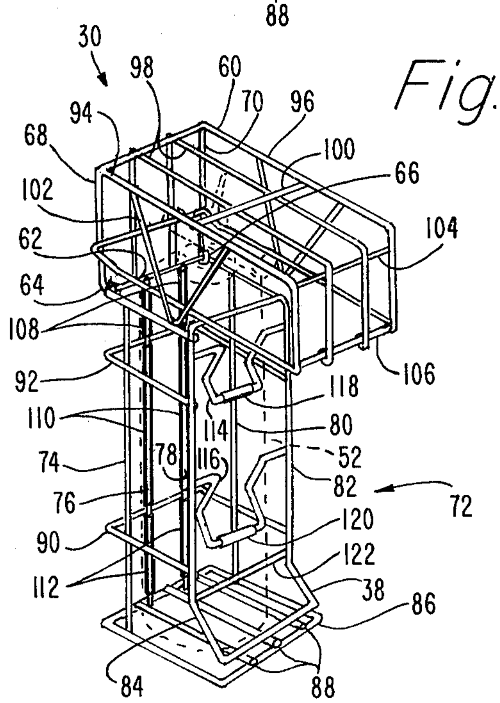
FIG. 5 is a perspective view of the frame of the oxygen caddy of FIG. 1 with an oxygen tank shown in shadow.
Figure 8:
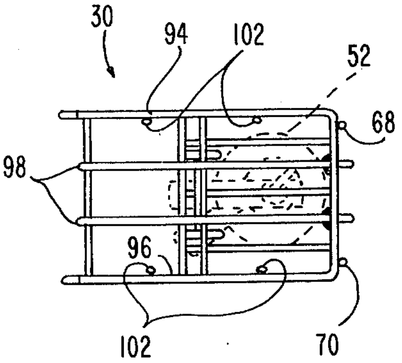
FIG. 8 is a top view of the frame of FIG. 5 with an oxygen tank shown in shadow.

With particular reference to FIG. 2, the top 14 of the case 12 is preferrably designed to open when the quick release buckle 24 is opened, in order to thereby provide immediate access to a cutoff valve 34 attached to a regulator 36 on top of an oxygen tank 52, which allows the emergency personnel to readily turn on the oxygen flow. The use of the quick release buckle 24 decreases the time required to administer oxygen to an individual in need thereof. It will be recognized by those skilled in the art that the type of cutoff valve 34 which is illustrated represents only one type of cutoff valve, and the use of this particular type of cutoff valve 34 is not critical to the present invention.

With continued reference to FIG. 2, the bottom of the oxygen caddy 10 of the preferred embodiment of the invention includes a base portion 38 which is broader, when viewed from the front or rear, than the remaining portions of the caddy 10. The purpose of the broadened base portion 38 is to stabilize the caddy 10 in order to prevent it from falling over when it is in use. Another feature of the preferred embodiment of the invention is the inclusion of sets of hook and loop fastening straps 37, 39, which are used to hold the shoulder strap 26 in a neatly folded manner when the oxygen caddy 10 is not in use.

With reference to FIGS. 1 and 2, in the preferred embodiment of the caddy 10 the support strap 25 is sewed the case 12 from a point 40 on the front of the case 12 to a point 42 on the rear of the case 12 in order to maximize the support which it provides. One end of the shoulder strap 26 is attached to the support strap 25, preferably by sewing, at a point 41 which is near the point 42. The other end of the shoulder strap 26 is attached to the adjustment buckle 28. The shoulder strap 26 loops through a support buckle 29 which is attached to the support strap 25. The carrying strap 27, in the preferred embodiment of the invention is sewed directly to the shoulder strap 26.

When the top 14 of the caddy 10 is open, as shown in FIG. 2, the top of the oxygen tank 52 and the pressure gauge 54 on the regulator 36 are exposed. Thus, the pressure gauge 54 may be readily observed in order to determine the quantity of oxygen remaining in the tank 52.

Figure 3:
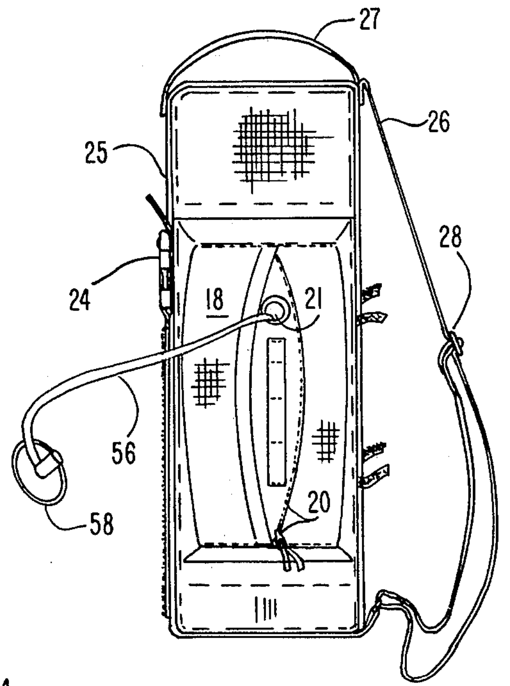
FIG. 3 is a view of the right side of the oxygen caddy of FIG. 1 showing the carrier with the pocket opened.

With particular reference to FIG. 3, with the side zipper 20 opened, an opening 21 in the side of the case 12 can be seen. The purpose of the opening 21 is to allow a hose 56 to pass from the regulator 36 on the oxygen tank 52 through the case 12 to one of the oxygen delivery means 58 which is normally stored in the pocket 16. The particular oxygen delivery means 58 which is illustrated is a demand valve. However, any other delivery means, such as an aspirator or an inhilator, could also be attached to the hose 56. If a three-way valve, such as the one identified above, is used on the oxygen regulator 36, then each of the three types of oxygen delivery means can be left attached so that any of them would typically be available for immediate use. In such case, one delivery means would be stored in one of the pockets 16, 18, and the other two delivery means would typically be stored in the other one of the pockets 18, 16.

Referring now to FIGS. 5–8, the frame 30 of the caddy 10 is shown with the case 12 removed. The frame 30 of the preferred embodiment of the invention is comprised of a series of welded rods which are arranged in a manner which protects the oxygen tank 52 (shown in shadow). However, the frame 30 could also be comprised of a formed material, such as metal or plastic which includes appropriate openings.

The frame 30 includes a protective cage 60 which is attached to the rear portion of a U-shaped horizontal support member 62 by hinges 64, 66. In the preferred embodiment of the frame 30, the protective cage 56 is comprised of a series of rods 68, 70 which are spaced from one another and connected together to form a protective housing. The hinges 64, 66 are comprised of portions of the rods 68, 70 which are formed around the horizontal cross member 62. Accordingly, the hinges 64, 66 have no moving parts, yet they allow the protective cage 60 to be opened, as shown in shadow of FIG. 7, so that the oxygen tank 52 may be inserted into the frame 30. In its closed position, the protective cage 60 prevents the tank 52 from coming out of the frame 30. The protective cage 60 is held in its closed position by the support strap 25 (shown in FIGS. 1–4) when the quick release buckle 24 is in its closed position.

In accordance with the preferred embodiment of the invention, the frame is also comprised of a tank holding portion 72. The tank holding portion 72 is comprised of vertical support members 74, 76, 78, 80, 82, 84. It further comprises a support base 86 having substantially parallel, horizontal members 88 welded thereon. The vertical support members 74, 76, 78, 80, are welded to the base 86. The vertical support members 82, 84 are joined by a horizontal lower portion which forms the base 38 and which is welded to the horizontal members 88.

U-shaped horizontal support members 90, 92, are welded to the vertical support members 74, 76, 78, 80, 82, 84, as is the member 62 to which the protective cage 60 is attached.

The protective cage 62 is comprised of substantially rectangular side members 94, 96 which comprise the sides of the cage 62. The side portions are joined by cross members 100, 104, 106, which are welded to the side members 94, 96. Additional support members are also welded to the cross members 100, 104, 106. Additional support for the protective cage 62 of the preferred embodiment of the invention comes from V-shaped members which are welded to the side members 94, 96.

The hinged protective cage 62 is an important feature of the present invention, as it allows an oxygen tank 52 to be readily inserted in, or removed from the frame 30 without removing the case 12. Tank retaining means 114, 116, are comprised of shaped rods, welded to the vertical members 82, 84. The tank retaining means 114, 116, together with a horizontal member 122, help form the tank holding portion 72. The tank retaining means 114, 116, include protective means, such as plastic tubes 118, 120 which prevent the retaining means 114, 116 from damaging an oxygen tank 52 inserted into the tank holding portion 72.

In the preferred embodiment of the invention, the tubes 118, 120 are placed over the retaining means 114, 116 before the retaining means 114, 116 are bent into shape and welded to the vertical members 82, 84. However, it is also possible to slit the tubes 118, 120 and insert them onto the retaining means 114, 116 at a later time. Similar protective tubes 108, 110, 112 are placed over the vertical support members 76, 78 in that manner.

In the preferred embodiment of the invention, the case 30 is held on the frame 12, in part, by hook and loop fasteners 35, as shown in FIG. 2.

As will be understood by those of ordinary skill in the art, the important features of the frame 30 are that it protects the tank 52 by enclosing it. Yet, it allows the tank 52 to be easily and readily inserted and removed without removing the case 12 from the frame. Finally, with all of these features, it remains light in weight. While these features are important aspects and features of the invention, various ones of them, or all of them, may be obtained by using a formed, solid frame, rather than the welded frame 30 of the preferred embodiment.

I claim:

1. An oxygen caddy which comprises:

(a) a rigid supporting frame adapted to hold and completely surround an oxygen tank together with its regulator and valve, said frame including a hinged top portion constructed to define a protective cage for a regulator attached to an oxygen tank within said frame;

(b) a fabric case into which said rigid supporting frame is placed, said case including at least one pocket in which oxygen delivery means may be stored, and an opening through said case into said at least one pocket, whereby a hose connecting an oxygen delivery means to an oxygen tank may extend through said opening in said case and into said pocket.

2. The oxygen caddy of claim 1 further comprising a shoulder strap.

3. The oxygen caddy of claim 2 wherein the shoulder strap includes means for adjusting its length.

4. The oxygen caddy of claim 2 wherein the shoulder strap includes means for holding said hinged protective cage closed.

5. The oxygen caddy of claim 4 wherein the means for holding said hinged protective cage closed is comprised of a quick release buckle.

6. The oxygen caddy of claim 2 wherein the shoulder strap includes means for holding small items thereon.

7. The oxygen caddy of claim 6 wherein said means for holding small items is comprised of hook and loop material on said shoulder strap.

8. The oxygen caddy of claim 1 in which said rigid supporting frame is comprised of metal rods which are welded together.

9. The oxygen caddy of claim 8 wherein the top of said frame includes means for retaining an oxygen tank lowered into it.

10. The oxygen caddy of claim 9 wherein the means for retaining an oxygen tank is comprised of spring type retaining members.

11. The oxygen caddy of claim 10 wherein said frame includes means for protecting an oxygen tank lowered into it.

12. The oxygen caddy of claim 11 wherein said means for protecting said oxygen tank comprises plastic tubes on said metal rods.

13. The oxygen caddy of claim 1 wherein said case is comprised of canvas.

14. The oxygen caddy of claim 1 wherein said case is comprised of nylon.

15. The oxygen caddy of claim 13 or claim 14 wherein said case includes two pockets.

16. The oxygen caddy of claim 1 wherein the bottom of said frame is formed into a wide, stable base.

* * * * *